United States Patent [19]

Peterson

[11] Patent Number: 5,906,623
[45] Date of Patent: *May 25, 1999

[54] LITHOTRIPSY SYSTEM

[75] Inventor: Francis C. Peterson, Prescott, Wis.

[73] Assignee: Boston Scientific Corporation, Natick, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/902,505

[22] Filed: Jul. 29, 1997

Related U.S. Application Data

[63] Continuation of application No. 08/570,087, Dec. 11, 1995, abandoned.

[51] Int. Cl.$^6$ .................................................. A61B 17/22
[52] U.S. Cl. .............................................. 606/128; 604/22
[58] Field of Search .................................. 606/128, 171, 606/127; 604/22

[56] References Cited

U.S. PATENT DOCUMENTS

| | | |
|---|---|---|
| 2,740,406 | 4/1956 | Tofflemire . |
| 3,447,476 | 6/1969 | Farris . |
| 3,543,590 | 12/1970 | Bergendal et al. . |
| 3,823,717 | 7/1974 | Pohlman et al. . |
| 4,227,532 | 10/1980 | Bluhm et al. ........................... 606/128 |
| 4,609,368 | 9/1986 | Dotson, Jr. ................................ 604/22 |
| 4,660,573 | 4/1987 | Brumbach . |
| 4,748,971 | 6/1988 | Borodulin et al. . |
| 4,907,572 | 3/1990 | Borodulin et al. . |
| 5,125,413 | 6/1992 | Baran ....................................... 606/171 |
| 5,160,336 | 11/1992 | Favre ....................................... 606/128 |
| 5,176,688 | 1/1993 | Narayan et al. . |
| 5,425,735 | 6/1995 | Rosen et al. ............................. 606/128 |
| 5,449,363 | 9/1995 | Brust et al. .............................. 606/128 |
| 5,540,702 | 7/1996 | Walz ........................................ 606/128 |

Primary Examiner—Michael A. Brown
Assistant Examiner—Justine R. Yu
Attorney, Agent, or Firm—Testa, Hurwitz & Thibeault, LLP

[57] ABSTRACT

A lithotripsy system, used to break calculi and stones, consisting of a flexible energy probe assembly, which can be inserted into a small and flexible endoscope, and an energy source. The flexible energy probe assembly consists of a target mass, an impact rod and a return spring. The energy source supplies an impact to the target mass which then transmits the energy from the impact rod to the stone. A return spring then restores the target mass and impact rod to their original position after each impact. The energy source can be a mechanical, electrical or pneumatic system.

2 Claims, 6 Drawing Sheets

LITHOTRIPSY SYSTEM

RELATED APPLICATIONS

This is a continuation of U.S. patent application Ser. No. 08/570,087, filed Dec. 11, 1995, now abandoned.

TECHNICAL FIELD

The present invention relates to a lithotripsy system for breaking physiologic calculi, generally referred to as "stones".

BACKGROUND ART

Many patients develop stones within their common bile, urinary, renal or ureteral systems. These stones may block ducts and cause great pain and therefore must be removed. Several approaches are available for treating such stones.

The traditional approach has been open surgery where multiple incisions are made to approach and remove the stone from the duct. This treatment results in a relatively long recovery period for the patient, and has fallen into disfavor.

Currently, extra-corporeal shock wave lithotripsy (ESWL) has become the treatment of choice for many patients. In these devices the patient is subjected to shock waves. The shock waves pass through the patients' skin and break up the stones. However, there are stones which cannot be removed by this technique because of their location, volume or composition. In general, these difficult stones are candidates for alternate surgical approaches.

Among the alternate lithotriptors are those which operate on electro-hydraulic, pneumatic and ultrasonic principles, as well as devices which use laser energy to fragment the stones. U.S. Pat. No. 5,160,336 to Favre and U.S. Pat. No. 5,449,363 to Brust et al. which disclose pneumatically driven devices which are useful alternatives to conventional open surgery. However, even with these devices, there is a need for a lithotripsy system which can deliver high energy to the stones and operate with small and flexible endoscopes.

SUMMARY

The lithotripsy system 10 of the present invention consist of a flexible energy probe assembly 12 which may be inserted into a small and flexible endoscope 18. This flexible energy probe assembly 12 is connected to an energy source 14 and control unit 32, and together these components comprise the lithotripsy system 10. Several embodiments of energy source 14 are taught including a pneumatic system 16, a manually power mechanical spring system 22 and an electro-mechanical system 20.

In use the physician uses the endoscope 18 to position the flexible energy probe assembly 12 in the patient and to observe the distal impact tip 50 of the flexible energy probe assembly 12 during the procedure. The energy source 14 is connected to the flexible energy probe assembly 12 and the physician activates the flexible energy probe assembly 12 through an appropriate control unit 32.

BRIEF DESCRIPTION OF THE DRAWINGS

The drawings show an illustrative and exemplary system and identical reference numerals refer to identical structure throughout the several views wherein.

DETAILED DESCRIPTION

Overview

Figure 1:
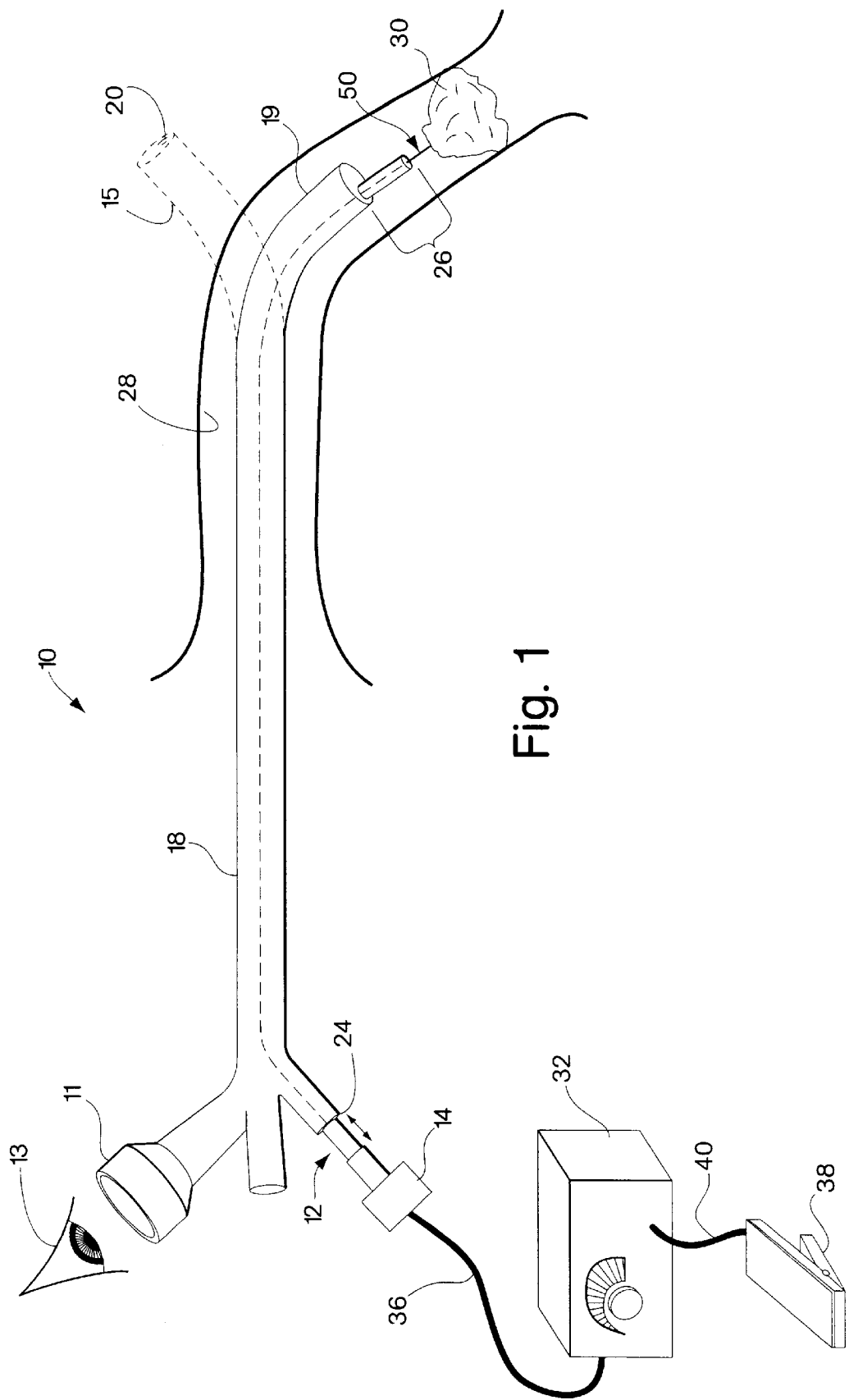
FIG. 1 is a schematic representation of the lithotripsy system 10.

FIG. 1 is an schematic representation of the overall lithotripsy system 10 assembled into an endoscope 18. The endoscope 18 has an eyepiece 11 for the observer or physician 13 and a flexible and steerable tip 19. The ability of the distal tip 19 to deflect is represented by outline 15. A lumen 20 is provided in the endoscope 18 to permit an instrument such as the flexible energy probe assembly 12 to be inserted into the endoscope 18 from the proximal port 24.

The energy probe assembly 12 is mounted in the endoscope lumen 20 so that it may be extended or retracted by the physician. In use, the physician will extend the impact rod 52 to the stone 30. This physician selected distance is indicated by reference numeral 26 in the figure. The endoscope 18 itself will typically be deflectable and or steerable by the physician. In use, the physician first inserts the endoscope 18 into the patient body cavity 28 and navigates the endoscope 18 to approach the stone 30. Next, the physician places the distal impact tip 50 of the energy probe assembly 12 on the stone 30 and actuates the control unit 32 to activate the energy probe assembly 12 which impacts and disintegrates the stone 30. In general a control unit 32 is connected to both the energy source 14 through an appropriate cable 36 and coupled to a foot operated control switch 38 through an appropriate cable 40 so that the physician can actuate the energy probe assembly 12 with his foot. Usually the physician uses his hands to control the endoscope 18.

Energy Probe

Figure 2:
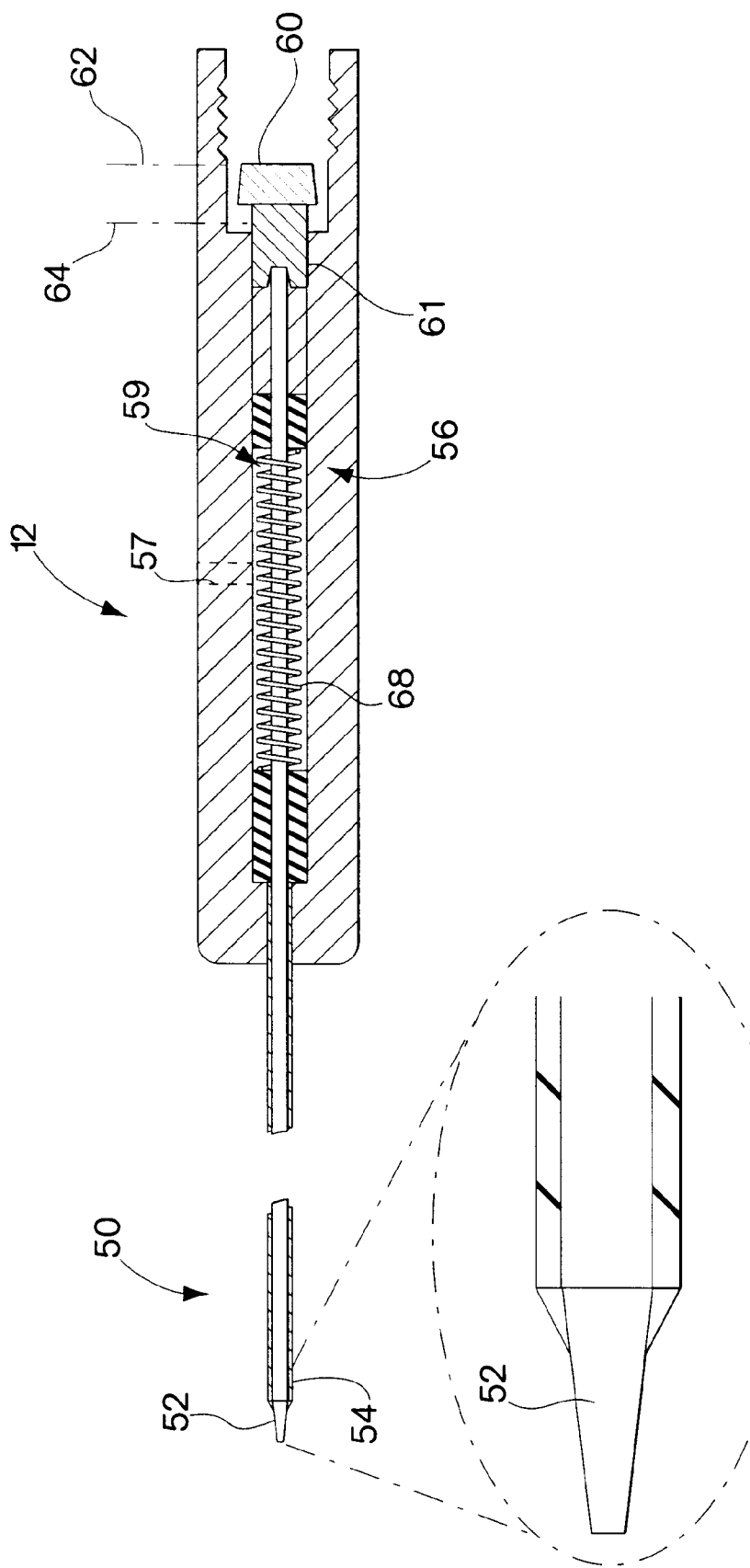
FIG. 2 is a schematic cross section of a portion of the flexible energy probe assembly 12.

The energy probe assembly 12 is a common element of the various embodiments of the system and is described in detail in connection with FIG. 2, FIG. 6, and FIG. 7. FIG. 2 is a simplified schematic cross section showing the energy probe assembly 12 in isolation. The figure shows the distal impact tip 50 of the flexible energy probe assembly 12 and shows that the impact rod 52 extends distally from the end of the impact rod sheath 54. In general, the overall length of the flexible energy probe assembly 12 is several feet, from the distal impact tip 50 to the proximal coupler body 56. The impact rod sheath 54 and the impact rod 52 together form a structure which can transmit impact energy from the target mass 60 attached to the impact rod 52 to the stone 30 (FIG. 1). In use the impact rod 52 and the target mass 60 reciprocate from a first position indicated by reference numeral 62 to a second position indicated by reference numeral 64. In each embodiment the energy source 14 supplies an impact on the target mass 60 to move the impact rod 52 and the attached target mass 60 from the first position to the second position. A return spring 68 is provided between the target mass 60 and the sheath 54 to permit the impact rod 52 to be restored to the initial or first position 62 after each impact. It is preferred to have the target mass 60 slide in a bore 61 formed in the coupler body 56. This bore aligns the target mass 60 and serves as a bearing surface.

The preferred material for both the impact rod 52 and the impact rod sheath 54 is Nitinol. Either the impact rod or the sheath, or both, may be made from this material. Nitinol is a substantially equiatomic alloy of nickel and titanium. In general, the impact rod 52 will have a small diameter between about 0.014 and 0.028 inches. It is also desirable to reduce or taper the diameter of the most distal segment of the impact rod 52 to enhance its flexibility. The optimal geometry for the energy probe assembly 12 must be determined based upon the mechanical properties of the companion endoscope 18 and the required energy level required at the distal impact tip 50. In general, rod diameter and stiffness must be balanced for best performance. Tests performed with the distal four inches of the energy rod tapered to a diameter of 0.018 inches has been found to be particularly effective. In general, the optimal impact rod 52 diameter and sheath dimensions will have to be determined experimentally for specific endoscopes and surgical procedures.

The energy probe assembly 12 should have an overall length which depends upon the particular endoscope 18 and procedure selected by the physician. However lengths (L) of approximately three feet are typical for the energy probe assembly 12.

Both pseudo-elastic and cold worked Nitinol can be used for the energy rod, but it appears preferable to use heavily cold worked Nitinol especially for smaller diameter energy rods, while it may be desirable to form the sheath from super elastic Nitinol in such applications. Although it is difficult to determine the precise amount of cold work in a piece of Nitinol, cold worked values above fifty percent are desirable for the impact rod 52. Lower values may be acceptable and perhaps desirable for the impact rod sheath 54. It should also be appreciated that either the impact rod 52 or the sheath 54 may be made from stainless steel or the like if lower flexibility and impact performance can be accepted. In particular, a Nitinol impact rod may be combined with a stainless steel sheath which includes a plastic distal section, as described later.

Mechanical Spring System

Figure 3:
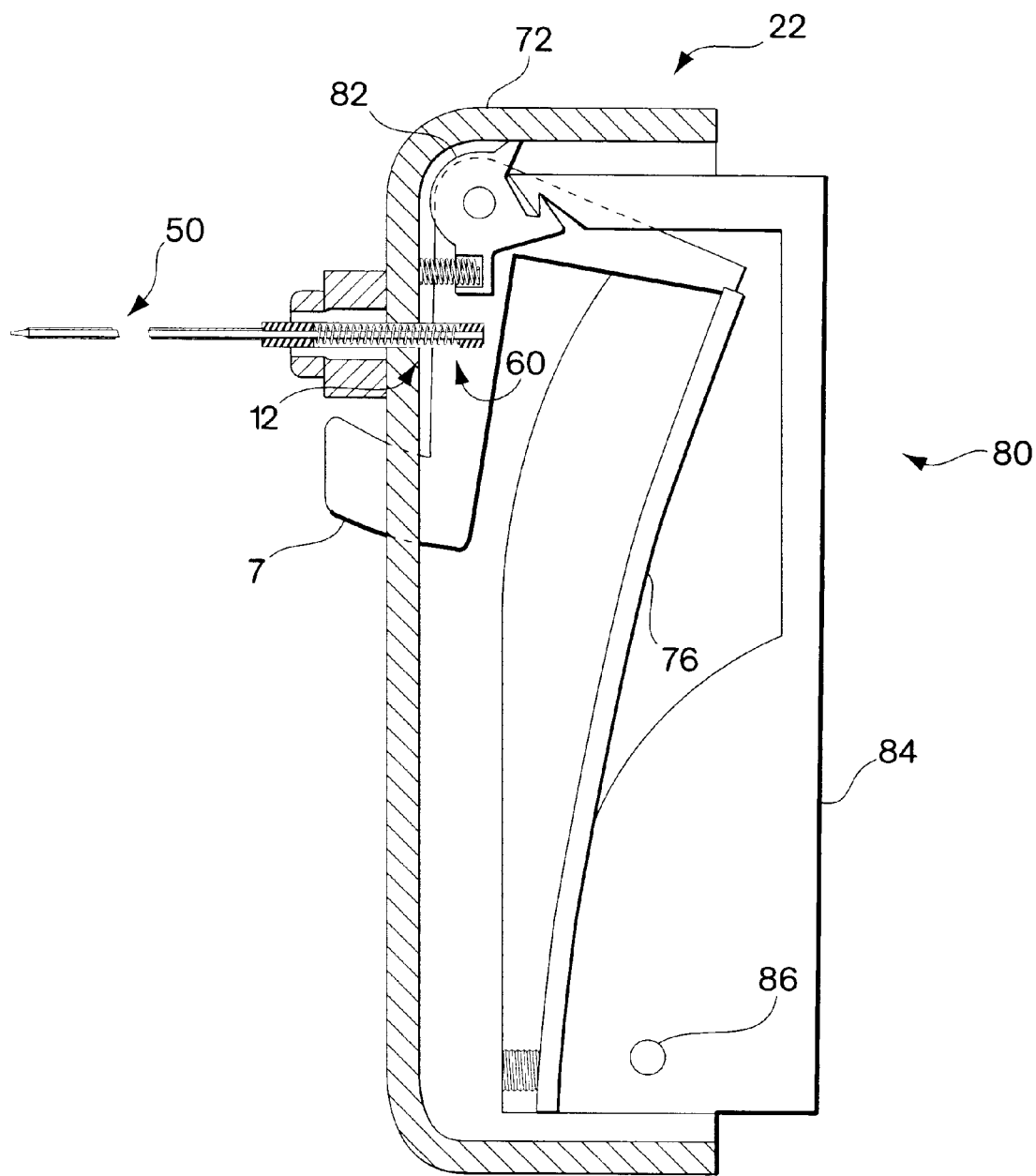
FIG. 3 is a schematic cross section of a mechanical spring system 22.

FIG. 3 is a schematic cross section of a manually operated mechanical spring system 22 for functioning as the energy source 14. The grip 72 is coupled to the energy probe assembly 12. It may be desirable to make the energy probe assembly 12 demountable from the grip 72. In operation, the spring 76 is released by the physician by squeezing the trigger 78. The spring then moves along impact path 80 and strikes the target mass 60 of the impact rod 52 transferring energy to the distal impact tip 50. The spring also impacts the latch paw 82 releasing the spring tension handle 84. To rearm the device for another impact the physician squeezes the spring tension handle 84 until it latches in the grip 72 by engaging the latch paw 82. The spring tension handle 84 pivots about a pivot axis 86 which controls the mechanical advantage of the device. It has been found that sufficient force can be supplied by relatively modest spring forces which are within the grip strength of a typical user. One advantage of this manually powered single shot device is that the entire product may be regarded as disposable. Additionally it has been found that many physicians prefer to apply a single impact at a time to ensure minimum trauma to the patient while removing stones.

Electromagnetic System

Figure 4:
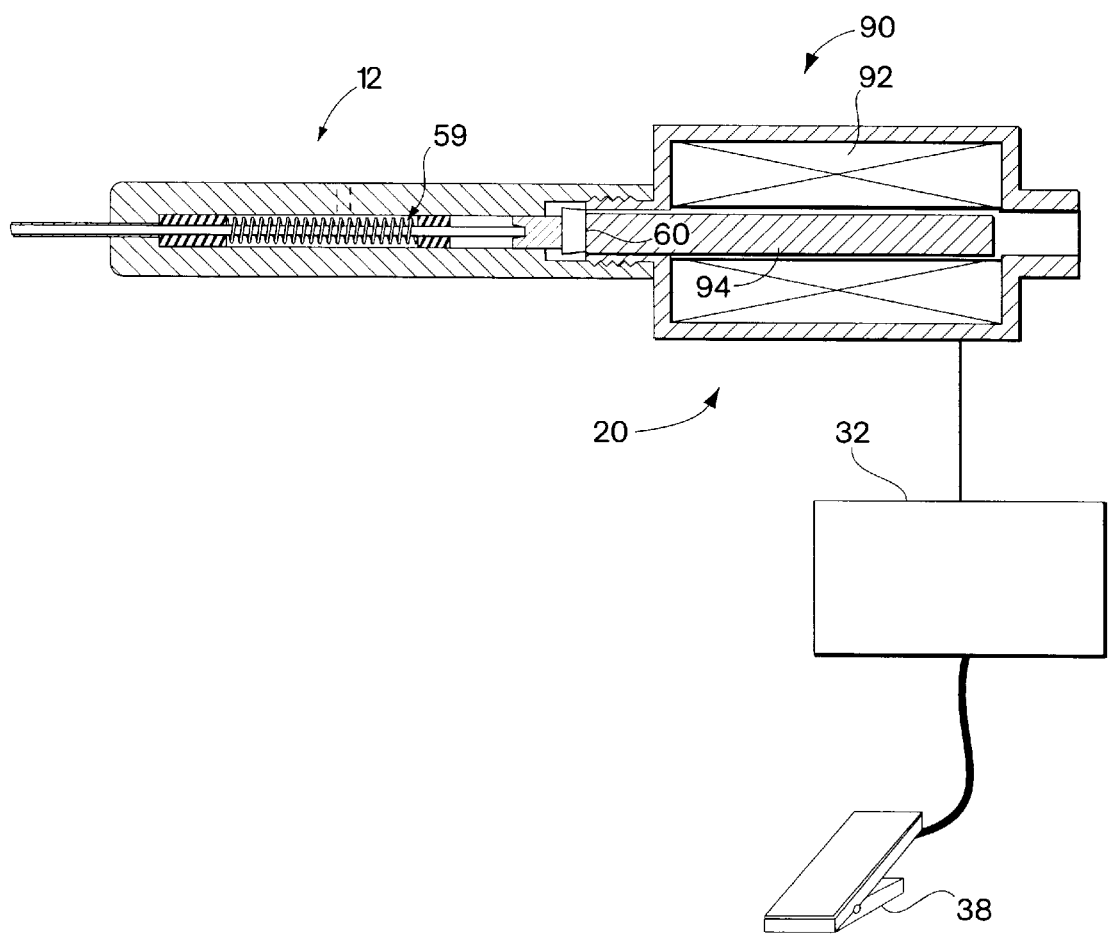
FIG. 4 is a schematic cross section of an electro-mechanical system 20.

FIG. 4 shows the energy source 14 in the form of a solenoid 90 which converts electrical current supplied to the coil 92 to a mechanical impact delivered to the target mass 30 attached to the energy rod 52 from an armature 94. In this embodiment the control unit 32 supplies electrical current to the solenoid 90 upon the actuation of the foot switch 38. It should be appreciated that the control unit may derive its electrical power from either internal batteries or conventional power lines. Detailed design parameters are not given as these are within the skill of the art in this area. One advantage of this type of energy source 20 for powering the flexible energy probe assembly 12 is that it is relatively small and easily controlled. One drawback is the necessary regulatory approval cycle required for electrically powered medical devices.

Pneumatic System

Figure 5:
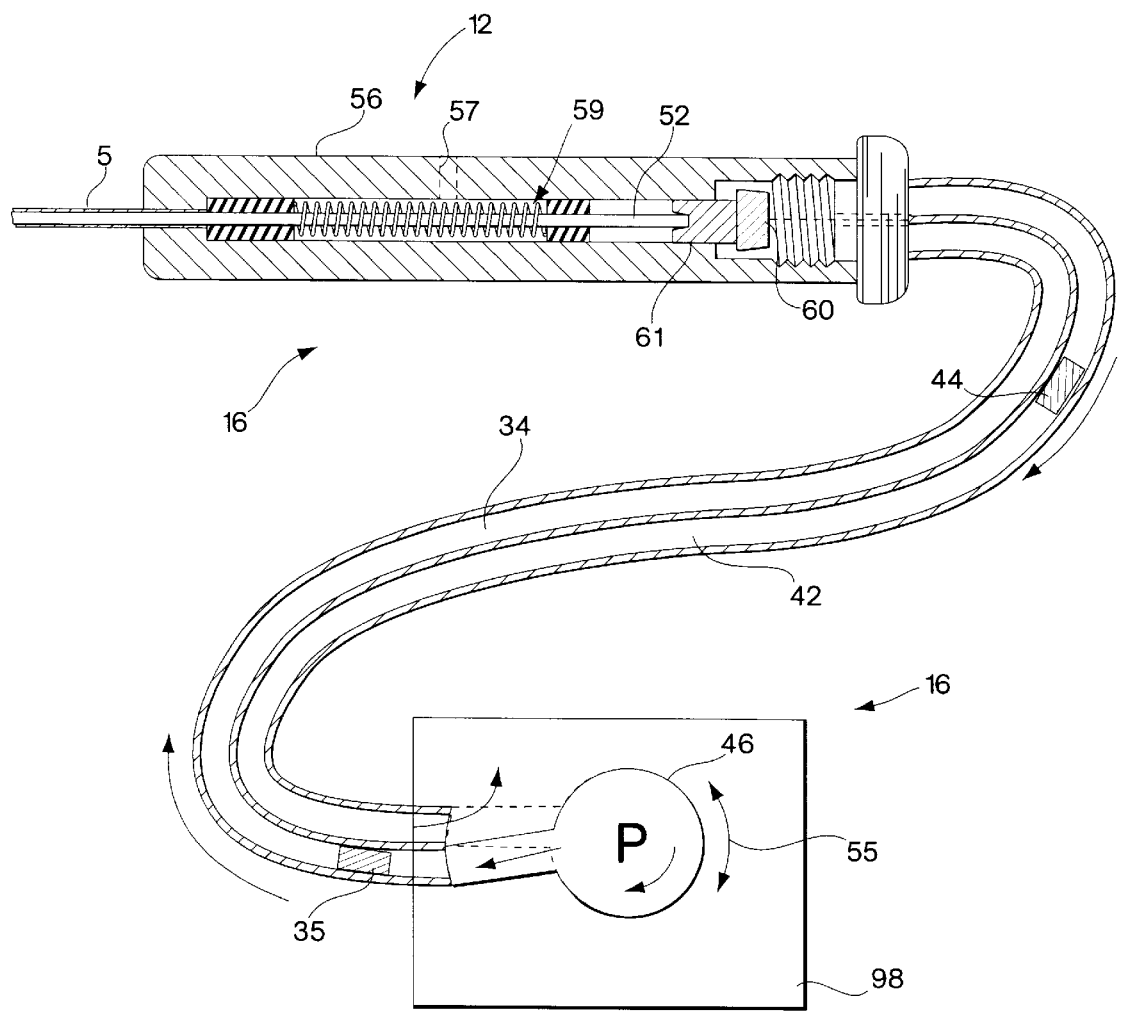
FIG. 5 is a schematic cross section of a pneumatic system 16

FIG. 5 is a schematic cross section of a pneumatic system 16 as the energy source 14. The pneumatic control unit 98 supplies pressurized air to one of two hammer tubes. The first hammer tube 34 contains a small cylindrical hammer 35 and the second hammer tube 42 contains a second hammer 44. As one hammer is driven into contact with the target mass 60 of the flexible energy probe assembly 12 by air pressure from the reservoir 46 the air pressure drives the companion hammer away from the target mass 60. After impact the pneumatic control unit 98 reverses the air pressure connections as indicated by arrow 55 and drives the alternate hammer into the target mass 60. This pneumatic oscillator cycle is illustrated in the figure. This cycle repeats and the multiple hammer impacts are transferred through the energy rod 52 to the location of the stone 30 where reciprocating motion of the distal impact tip 50 breaks up the stone 30 (FIG. 1).

This lithotripsy system 10 is preferably powered pneumatically from a remote source of gas pressure such as a hospital pressurized air supply. A bottle of compressed gas may be readily substituted where a suitable hospital air supply is unavailable. Both of these air supplies is shown schematically by reservoir 46.

In general the pneumatic control unit 98 contains a collection of valves and pneumatic switches which form the pneumatic oscillator, the detail design of which is within the ordinary skill in this art. The operating frequency is adjusted through the use of pneumatic valves which may be a physician adjustable parameter. Thus, in operation, hammer 35 may be launched from the control unit 98 and may be accelerated toward the target mass 60 by pressurizing the hammer tube 34 from the reservoir 46. Air returning from the target mass 60 drives the second hammer 44 toward the pneumatic control unit 98. The pneumatic unit control 98 vents the companion hammer tube and the air pressure drops down to the atmosphere to facilitate the return of the second hammer 44 to the pneumatic control unit 98. Next, the pneumatic unit control 98 pressurizes the first hammer tube 34 and vents the companion second hammer tube 42 and the hammer cycle repeats again.

Consequently when gas pressure is supplied to the first hammer tube 34, the first hammer 35 is accelerated to a high speed and moves rapidly in the distal direction. Ultimately the first hammer 35 impacts the target mass 60 and transfers its kinetic energy to the target mass 60. The elastic collision transfers momentum to the impact rod 52 which in turn impacts the stone 30. The actual motion of the impact rod 40 is believed to be quite complex but involves a reciprocating motion of the distal impact tip 50. The motion of the first hammer 35 and gas within the first and second hammer tubes drives the second hammer 44 in the proximal direction.

The volume 59 "behind" the target mass 60 within the coupler body 56, is vented to the atmosphere by a vent 57 formed in the coupler body 56. This vent 57 prevents the formation of a pneumatic spring which would otherwise tend to cushion the impacts supplied to the distal impact tip. Also the vent 57 limits the passage of compressed air down the energy probe assembly.

Figure 6:
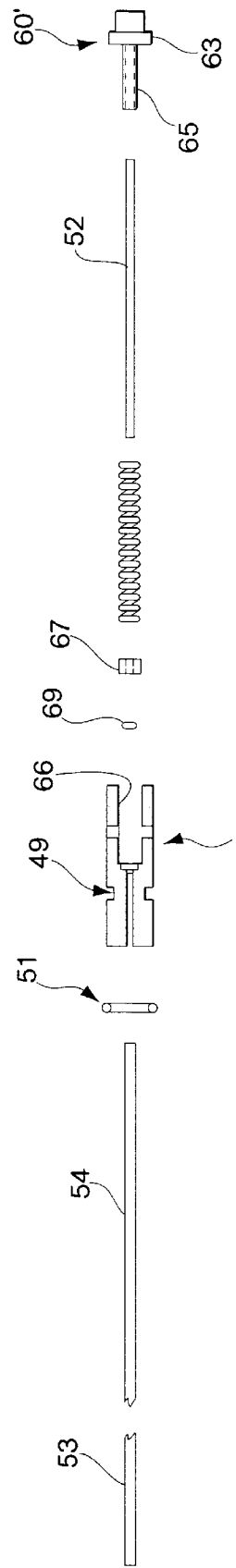
FIG. 6 is an exploded assembly drawing of an alternate flexible energy probe assembly 12.

FIG. 6 shows an exploded assembly drawing of an alternate flexible energy probe assembly 12. In this figure the target mass 60' includes a flange 63 which is sized to bottom out on the coupler body to limit the excursion of the attached impact rod 52. The target mass 60' also includes an elongate cylindrical bearing surface 65 which cooperates with the bore 66 formed in the coupler body 56 to position the target mass for reciprocating motion in the coupler body 56. A bushing 67 and O-ring 69 are positioned in the coupler body 56 and cooperate together to prevent gas from leaking into the impact rod sheath 54. An optional teflon sheath 53 may be used to extend an exemplary stainless steel or Nitinol sheath 54 to increase flexibility for use with an endoscope.

Figure 7:
FIG. 7 is an assembly drawing of an alternate flexible energy probe assembly 12.

FIG. 7 is an assembly drawing of the alternate flexible energy probe assembly 12 shown in FIG. 6. In this view the contact between the coupler body 56 and the flange 63 can be seen. An O-ring 51 may be positioned in groove 49 to facilitate connection of the flexible energy probe 12 to the energy source 14. This O-ring may further limit gas flow along the length of the assembly. It is preferable to vent the coupler body 56 to ensure that gas pressure does not build up within the coupler body 56.

Having thus described the invention it should be apparent that many changes may be made to the device without departing from the scope of the invention as set forth in the claims.

What is claimed is:

1. A lithotripsy system, comprising:
   an energy probe assembly in combination with an energy source;
   said energy probe assembly including:
      a coupler body for connection to said energy source;
      a target mass located for reciprocating motion within said coupler body, said target mass adapted to receive impacts from said energy source;
      an elongate impact rod coupled to said target mass;
      an impact rod sheath surrounding at least a portion of said impact rod; said impact rod and impact rod sheath together forming a distal impact tip; and
      a return spring mounted between said target mass and said coupler body to bias said impact rod into a first position;
   said energy source including:
      a first hammer tube containing a first hammer and having a first end and a second end;
      a second hammer tube containing a second hammer and having a first end and a second end;
      a pneumatic oscillator;
      said first and second hammer tubes being connected at the first ends to said pneumatic oscillator and at the second ends to said coupler body;
      said pneumatic oscillator alternating between (i) pressurizing said first hammer tube and venting said second hammer tube thereby driving said first hammer into contact with said target mass and (ii) pressurizing said second tube and venting said first hammer tube thereby driving said second hammer into contact with said target mass, whereby the impact of said first and second hammers on said target mass transfers energy through said impact rod.

2. The lithotripsy system of claim 1 wherein said pneumatic oscillator alternates between (i) pressurizing said first hammer tube and venting said second hammer tube thereby driving said first hammer toward said coupler body and driving said second hammer toward said pneumatic oscillator and (ii) pressurizing said second hammer tube and venting said first hammer tube thereby driving said second hammer toward said coupler body and driving said first hammer toward said pneumatic oscillator.

* * * * *